(12) United States Patent
Zhang et al.

(10) Patent No.: US 11,680,102 B2
(45) Date of Patent: Jun. 20, 2023

(54) ANTI-BAFF RECEPTOR ANTIBODIES AND USES THEREOF

(71) Applicants: YINNUOLAI BIOTECH LTD., Guangdong (CN); CITY OF HOPE, Duarte, CA (US)

(72) Inventors: Jianbing Zhang, Guangdong (CN); Hong Qin, Upland, CA (US); Larry W. Kwak, Pasadena, CA (US)

(73) Assignees: Yinnuolai Biotech Ltd., Guangzhou (CN); City of Hope, Duarte, CA (US)

( * ) Notice: Subject to any disclaimer, the term of this patent is extended or adjusted under 35 U.S.C. 154(b) by 107 days.

(21) Appl. No.: 17/179,467

(22) Filed: Feb. 19, 2021

(65) Prior Publication Data
US 2021/0261676 A1    Aug. 26, 2021

(51) Int. Cl.
*C07K 16/28*    (2006.01)

(52) U.S. Cl.
CPC ...... *C07K 16/2878* (2013.01); *C07K 2317/21* (2013.01); *C07K 2317/24* (2013.01); *C07K 2317/92* (2013.01)

(58) Field of Classification Search
CPC ................. C07K 16/2878; C07K 2317/21
See application file for complete search history.

(56) References Cited

U.S. PATENT DOCUMENTS

| 10,577,421 | B2 * | 3/2020 | Fang ............... C07K 16/2827 |
| 2016/0011217 | A1 | 1/2016 | Matsumura et al. |
| 2019/0225687 | A1 | 7/2019 | Fang et al. |

FOREIGN PATENT DOCUMENTS

| WO | 2017214167 A1 | 12/2017 | |
| WO | WO-2020172440 A1 * | 8/2020 | ............. A61K 35/17 |

OTHER PUBLICATIONS

He et al., (Lyhmphoma B Cells Evade Apoptosis through the TNF Family Members BAFF/BLyS and APRIL, 2004, The Journal of Immunology, vol. 172, Issue 5, pp. 3268-3279 (Year: 2004).*
Hengeveld and Kersten (B-cell activating factor in the pathophysiology of multiple myeloma: a target for therapy?, 2015, Blood Cancer Journal, vol. 5, e282, pp. 1-8). (Year: 2015).*
Endo et al., BAFF and APRIL support chronic lymphocytic leukemia B-cell survival through activation of the canonical NF-κB pathway, 2007, Blood, vol. 109, No. 2, pp. 703-710 (Year: 2007).*
International Search Report and Written Opinion dated May 21, 2021 in International Application No. PCT/US2021/018657.

* cited by examiner

*Primary Examiner* — Daniel E Kolker
*Assistant Examiner* — Brittney E Donoghue
(74) *Attorney, Agent, or Firm* — Ice Miller LLP

(57) ABSTRACT

Anti-BAFF-R antibodies and antigen-binding fragments thereof with potentially high stability and low immunogenicity are described. Also described are nucleic acids encoding the antibodies, compositions comprising the antibodies, methods of producing the antibodies, and methods of using the antibodies for treating or preventing diseases, such as cancer.

11 Claims, 7 Drawing Sheets

Specification includes a Sequence Listing.

8. V-REGION protein display

```
                         FR1-IMGT                    CDR1-IMGT             FR2-IMGT         CD
                          (1-26)                      (27-38)               (39-55)
         1       10        20                30         40         50
         .........|.........|.........|.........|.........|.........|.........
H90-11                DIQMTQSPDSLAVSLGERATINCKSS  QSVLYSSNNKNY  LAWYQQKPGQPPKLLIY  WA
Z00023 Homsap IGKV4-1*01 F  DIVMTQSPDSLAVSLGERATINCKSS QSVLYSSNNKNY  LAWYQQKPGQPPKLLIY  WA
                              Q R2-IMGT                  FR3-IMGT
         (56-65)                  (66-104)
         60        70        80        90       100
         .........|.........|.........|.........|.........
H90-11              S IRESGVP.DRFSGSG..SGTDFTLTISSLQPEDFATYYC QQSYS
Z00023 Homsap IGKV4-1*01 F  S TRESGVP.DRFSGSG..SGTDFTLTISSLQAEDVAVYYC QQYYSTP
                         I                                  P F T     S
```

FIG. 1A

ANTI-BAFF RECEPTOR ANTIBODIES AND USES THEREOF

CROSS REFERENCE TO RELATED APPLICATION

This application claims priority under 35 U.S.C. § 119(c) to International Application No. PCT/CN2020/076131, filed on Feb. 21, 2020, the disclosure of which is incorporated herein by reference in its entirety.

FIELD OF THE INVENTION

This invention relates to monoclonal anti-B-cell activating factor (BAFF) receptor antibodies, nucleic acids and expression vectors encoding the antibodies, recombinant cells containing the vectors, and compositions comprising the antibodies. Methods of making the antibodies, and methods of using the antibodies to treat diseases, including cancer, are also provided.

REFERENCE TO SEQUENCE LISTING SUBMITTED ELECTRONICALLY

This application contains a sequence listing, which is submitted electronically via EFS-Web as an ASCII formatted sequence listing with a file name "065815.1US1 Sequence Listing" and a creation date of Feb. 16, 2021 and having a size of 10 kb. The sequence listing submitted via EFS-Web is part of the specification and is herein incorporated by reference in its entirety.

BACKGROUND OF THE INVENTION

Monoclonal antibody immunotherapy can be highly successful in the treatment of cancers, and, in particular, the treatment of hematologic malignancies. However, monoclonal antibody treatment alone is not curative, and the emerging resistance can be a problem. One target for the treatment of hematologic malignancies is CD20, which can be targeted with rituximab. Resistance to rituximab has been observed, and is thought to be caused by multiple mechanisms, including, for example, downregulation of CD20 expression.

An alternative target on B-cell tumors is the B-cell-activating factor (BAFF) receptor, a TNF receptor superfamily member specifically involved in B lymphocyte development and B-cell survival. BAFF receptor is expressed almost exclusively on B cells, and the surface expression of BAFF receptor has been identified in various human B-cell lymphomas. Given that much of the signaling of BAFF and the BAFF receptor is known, it remains an attractive target for B-cell lymphomas, and, therefore, anti-BAFF receptor monoclonal antibodies (mAbs) can be used as potential anti-cancer therapeutics.

BRIEF SUMMARY OF THE INVENTION

Provided herein are isolated monoclonal antibodies or antigen-binding fragments thereof that specifically bind B-cell activating factor (BAFF) receptor. The isolated monoclonal antibodies or antigen-binding fragments thereof can have increased stability and/or reduced immunogenicity when compared to previously disclosed anti-BAFF receptor antibodies or antigen binding fragments thereof.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of SEQ ID NOs: 3, 4, 5, 6, 7, and 8, respectively, wherein the antibody or antigen-binding fragment thereof specifically binds BAFF receptor, preferably human BAFF receptor.

In certain embodiments, the isolated monoclonal antibody or antigen-binding fragment thereof comprises a heavy chain variable region having a polypeptide sequence at least 95%, at least 96%, at least 97%, at least 98%, or at least 99% identical to SEQ ID NO:1, and a light chain variable region having a polypeptide sequence at least 95%, at least 96%, at least 97%, at least 98%, or at least 99% identical to SEQ ID NO:2.

In certain embodiments, the isolated monoclonal antibody or antigen-binding fragment thereof comprises a heavy chain variable region having the polypeptide sequence of SEQ ID NO:1, and a light chain variable region having the polypeptide sequence of SEQ ID NO:2.

In certain embodiments, the isolated monoclonal antibody or antigen-binding fragment thereof is human or humanized.

In certain embodiments, the isolated monoclonal antibody or antigen-binding fragment thereof binds to BAFF receptor and is capable of inducing effector-mediated tumor cell lysis.

Also provided are isolated nucleic acids encoding the monoclonal antibodies or antigen-binding fragments thereof of the invention.

Also provided are vectors comprising the isolated nucleic acids encoding the monoclonal antibodies or antigen-binding fragments thereof of the invention.

Also provided are host cells comprising the vectors comprising the isolated nucleic acids encoding the monoclonal antibodies or antigen-binding fragments thereof of the invention.

In certain embodiments, provided is a pharmaceutical composition comprising the isolated monoclonal antibody or antigen-binding fragment thereof of the invention and a pharmaceutically acceptable carrier.

Also provided are methods of treating cancer in a subject in need thereof, comprising administering to the subject the pharmaceutical compositions of the invention. In certain embodiments, the cancer is a lymphoma, a leukemia, or a myeloma. The cancer can be, but is not limited to, a non-Hodgkin's lymphoma (NHL), an acute lymphocytic leukemia (ALL), a chronic lymphocytic leukemia (CLL), a chronic myelogenous leukemia (CIVIL), a multiple myeloma (MM), an acute myeloid leukemia (AML), and other liquid tumors. The non-Hodgkin's lymphoma (NHL) can, for example, be a mantle cell lymphoma, a follicular lymphoma, a diffuse large B-cell lymphoma, a marginal zone lymphoma, or a Burkitt's lymphoma.

Also provided are methods of producing the monoclonal antibody or antigen-binding fragment thereof of the invention. The methods comprise culturing a cell comprising a nucleic acid encoding the monoclonal antibody or antigen-binding fragment thereof under conditions to produce the monoclonal antibody or antigen-binding fragment thereof and recovering the monoclonal antibody or antigen-binding fragment thereof from the cell or culture.

Also provided are methods of producing a pharmaceutical composition comprising the monoclonal antibody or antigen-binding fragment of the invention. The methods comprise combining the monoclonal antibody or antigen-binding fragment with a pharmaceutically acceptable carrier to obtain the pharmaceutical composition.

Also provided are methods of determining a level of BAFF receptor in a subject. The methods comprise (a) obtaining a sample from the subject; (b) contacting the sample with an isolated monoclonal antibody or antigen-binding fragment thereof of the invention; and (c) determining a level of BAFF receptor in the subject. The sample can, for example, be a tissue sample or a blood sample. The tissue sample can, for example, be a cancer tissue sample.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIGS. 1A-1B show alignments human germ line light chain Ig sequences (IGKV4-1*01 (SEQ ID NO:17); IGKV3-11*01 (SEQ ID NO:19)) with light chain sequences of H90-11 mAb (FIG. 1A) (SEQ ID NO:2) and H90-5 mAb (FIG. 1B) (SEQ ID NO:10).

DETAILED DESCRIPTION OF THE INVENTION

Figure 1B:
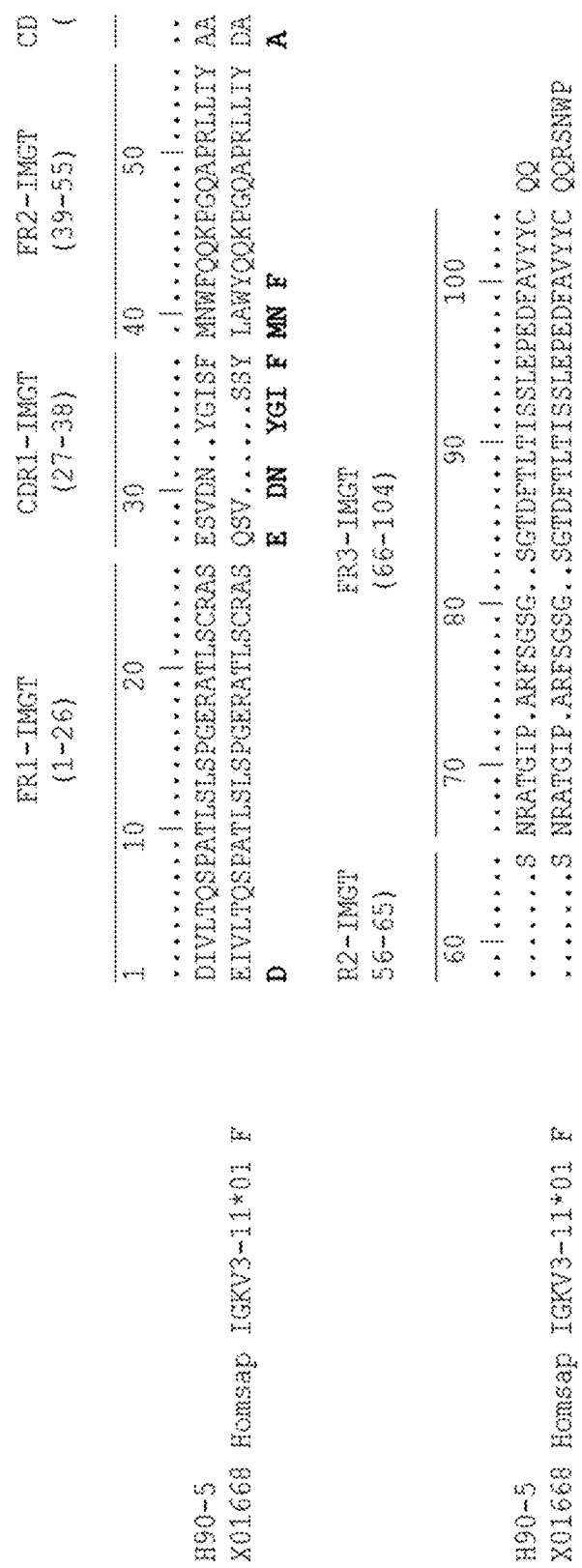
Figure 2A:
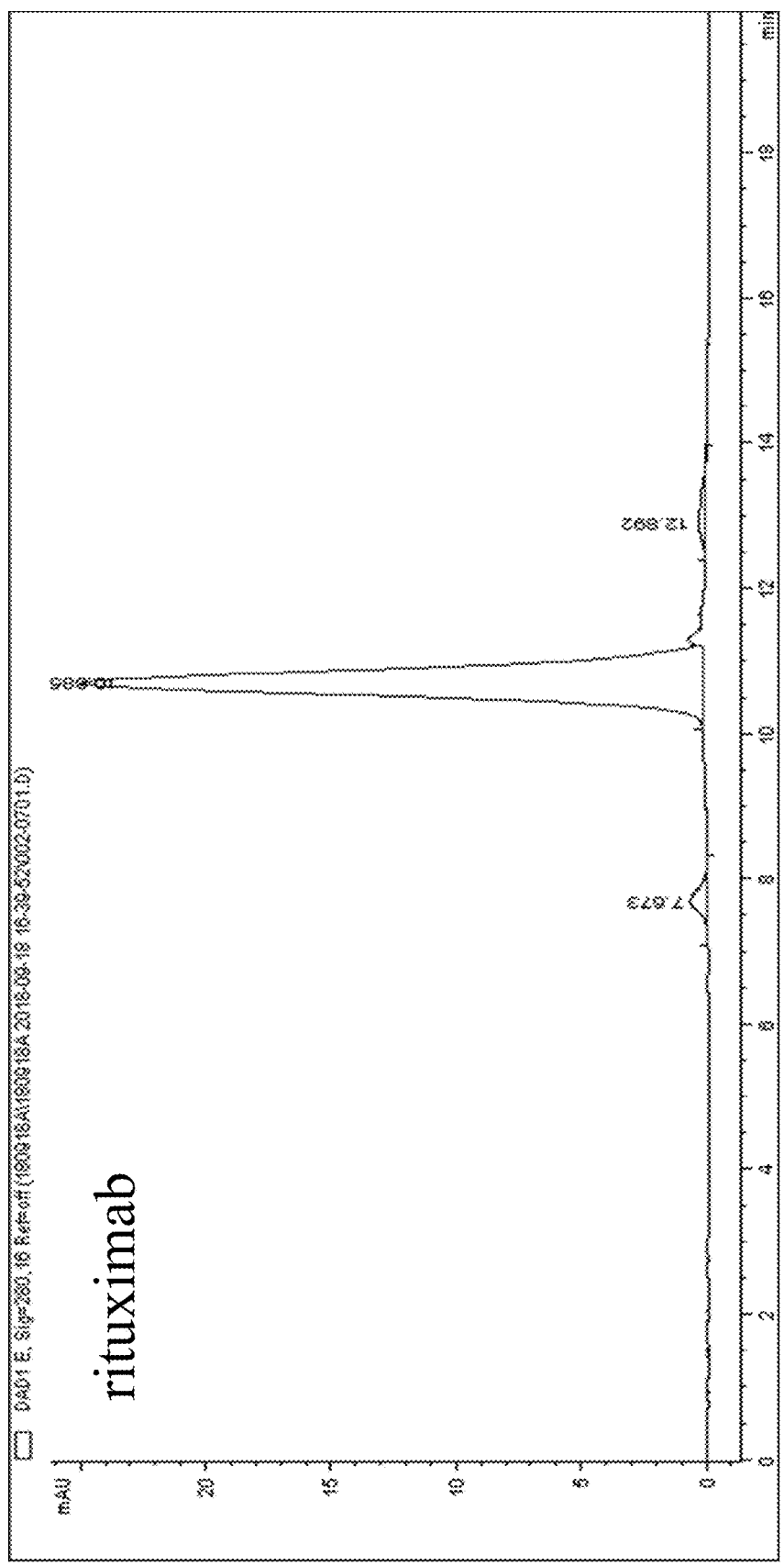
FIGS. 2A-2D show graphs demonstrating the results of the SMAC-HPLC experiment to determine Retention Time (RT) for Rituxan (FIG. 2A), C90 (FIG. 2B), H90-5 (FIG. 2C), and H90-11 (FIG. 2D).
Figure 2B:
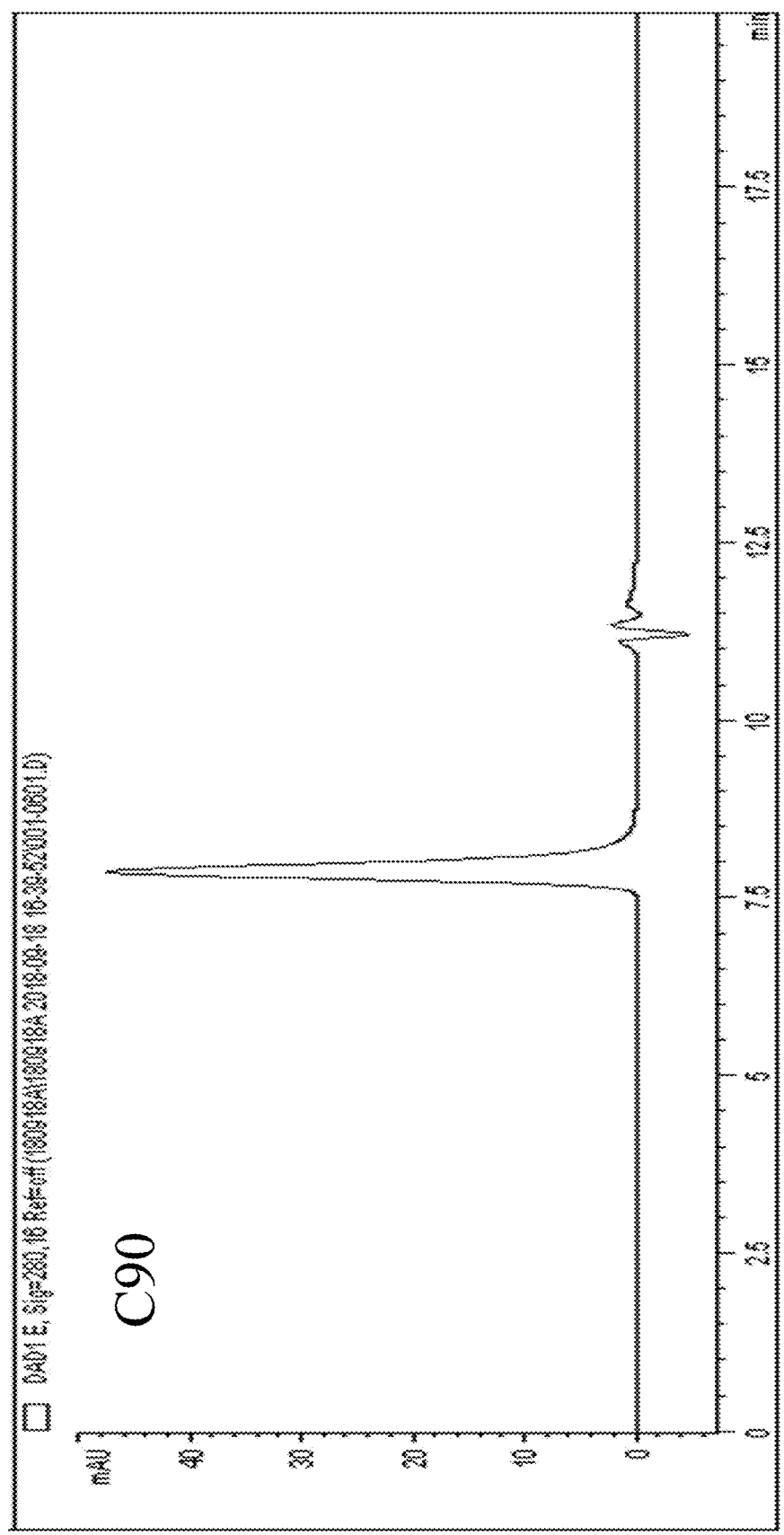
Figure 2C:
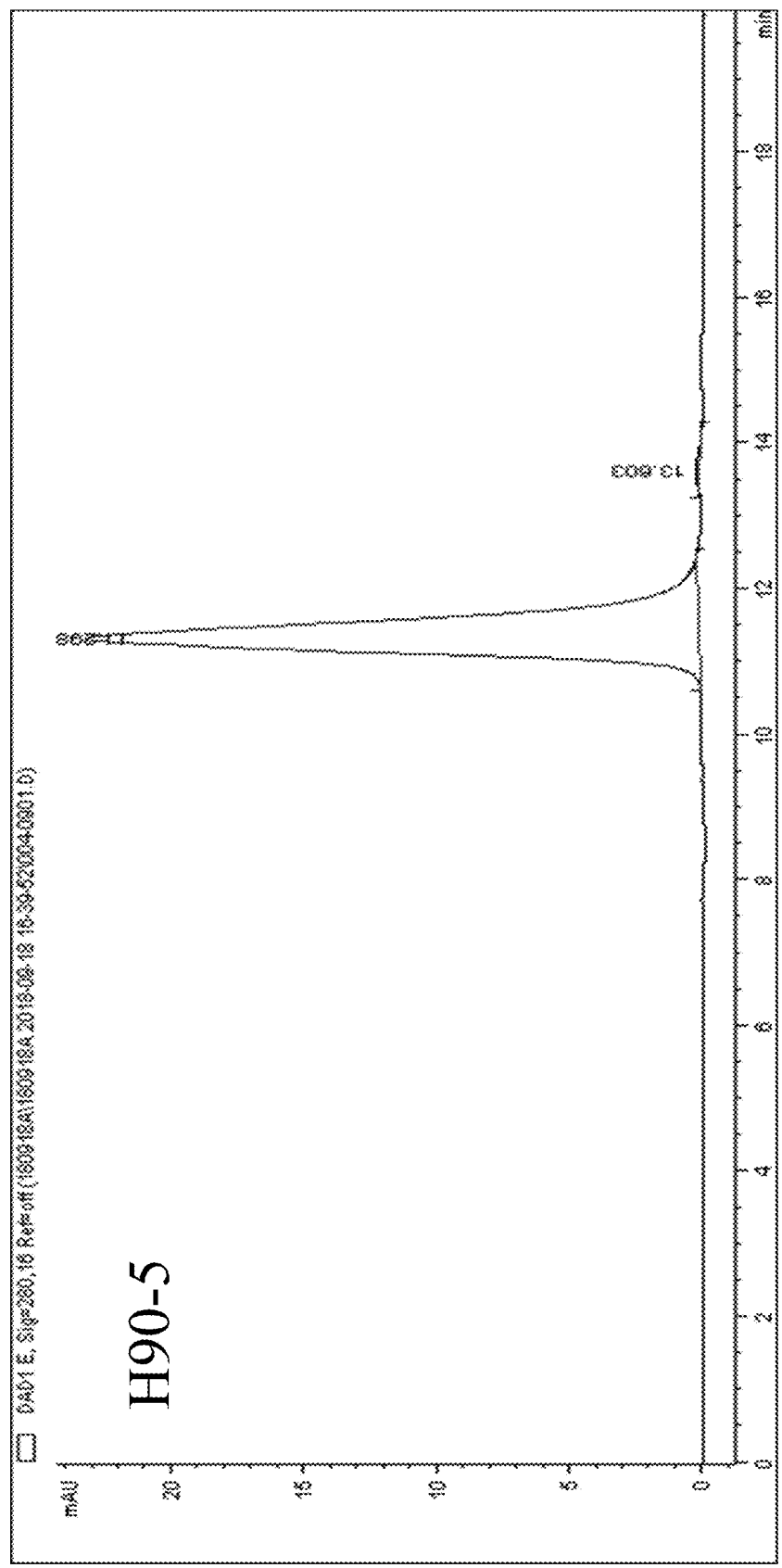
Figure 2D:
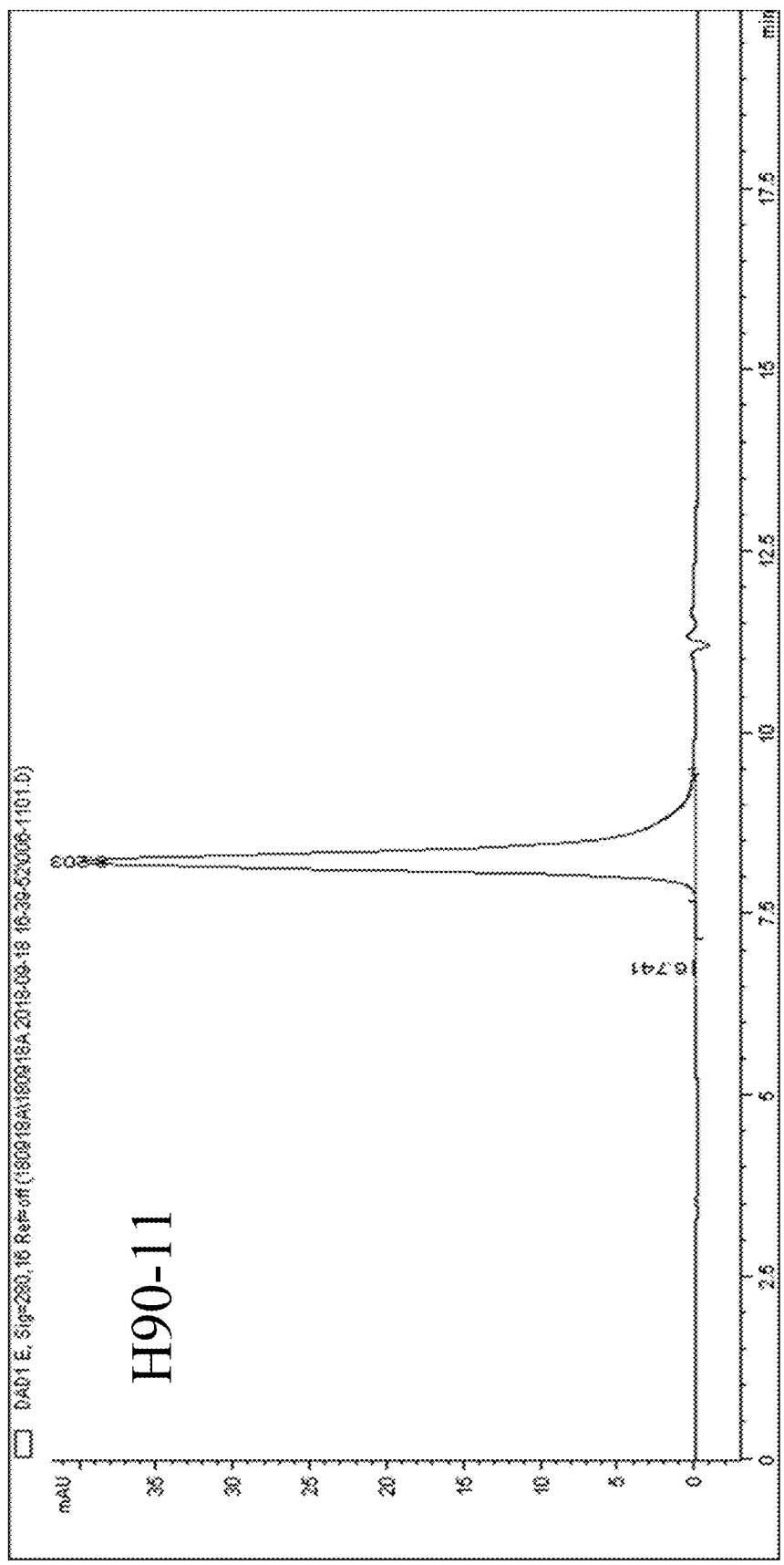

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of" or variations such as "consist of" or "consisting of," as used throughout the specification and claims, indicate the inclusion of any recited integer or group of integers, but that no additional integer or group of integers can be added to the specified method, structure, or composition.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The terms "identical" or percent "identity," in the context of two or more nucleic acids or polypeptide sequences (e.g., anti-BAFF receptor antibodies and polynucleotides that encode them, BAF receptor polypeptides and BAFF receptor polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed polypeptide can be within the cytoplasm of a host cell, into the extracellular milieu such as the growth medium of a cell culture or anchored to the cell membrane.

As used herein, the terms "peptide," "polypeptide," or "protein" can refer to a molecule comprised of amino acids and can be recognized as a protein by those of skill in the art. The conventional one-letter or three-letter code for amino acid residues is used herein. The terms "peptide," "polypeptide," and "protein" can be used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated polypeptide refers to one that can be administered to a subject as an isolated polypeptide; in other words, the polypeptide may not simply be considered "isolated" if it is adhered to a column or embedded in a gel. Moreover, an "isolated nucleic acid fragment" or "isolated peptide" is a nucleic acid or protein fragment that is not naturally occurring as a fragment and/or is not typically in the functional state.

Antibodies

The application generally relates to isolated anti-BAFF receptor antibodies, nucleic acids and expression vectors encoding the antibodies, recombinant cells containing the vectors, and compositions comprising the antibodies. Methods of making the antibodies, and methods of using the antibodies to treat diseases including cancer are also provided. The antibodies of the invention possess one or more desirable functional properties, including but not limited to high-affinity binding to BAFF receptor, high specificity to BAFF receptor, increased stability, and reduced immunogenicity.

The anti-BAFF receptor antibodies described herein are designed for optimal developability to proceed through clinical trials and for approval as a drug for treating or preventing cancer in a subject in need thereof. The predominant feature of the anti-BAFF receptor antibodies is target binding with minimal to no cross-reactivity with off target molecules; however, once an antibody has been found that attains the desired potency upon binding the appropriate target (e.g., the BAFF receptor), the developability of the antibody is of critical importance. Developability of an anti-BAFF receptor antibody can be determined by analyzing multiple properties of the anti-BAFF receptor antibody, which include, but are not limited to, expression of the antibody, solubility of the antibody, covalent integrity of the antibody, conformational and colloidal stability of the antibody, polyspecificity of the antibody, and immunogenicity of the antibody. Anti-BAFF receptor antibodies with optimal developability demonstrate high-level expression, high solubility, high covalent integrity, high conformational and colloidal stability, low polyspecificity, and low immunogenicity. Developability and the biophysical properties of antibodies are discussed, e.g., in Jain et al., PNAS 114(5): 944-949 (2017).

In a general aspect, the invention relates to isolated monoclonal antibodies or antigen-binding fragments thereof that specifically bind BAFF receptor and have the desired features in regard to improved stability and reduced potential immunogenicity. Such antibodies will have higher manufacturability and can cause less anti-drug immune response in subjects (e.g., human subjects).

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to BAFF receptor is substantially free of antibodies that do not bind to BAFF receptor). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that can be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multi-specific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on BAFF receptor and the second epitope is located on PD-1, PD-L1, CTLA-4, EGFR, HER-2, CD19, CD20, CD33, CD47, CD73, CD3 and/or other tumor associated immune suppressors or surface antigens.

As used herein, the term "BAFF receptor" refers to B-cell activating factor (BAFF) receptor, also known as tumor necrosis factor receptor superfamily member 13C (TNFRSF13C and BLyS receptor 3 (BR3), which is a membrane protein of the TNF receptor superfamily which recognizes BAFF, an essential factor for B cell maturation and survival. BAFF receptor is an atypical representative of the TNF-receptor super-family, as members of the TNF-receptor super-family typically are characterized by several extracellular cysteine-rich domains (CRDs), which serve for ligand binding as well as ligand-independent assembly of receptor monomers, dimers, trimers, or multimers. Unlike most TNF-R family members, BAFF receptor contains only a partial CRD, which serves for ligand binding as well as for self-assembly. BAFF receptor expression starts when the immature B cells develop to transitional B cells, which then receive BAFF receptor-dependent pro-survival signals to rescue them from premature cell death. BAFF receptor expression has been observed in various stages of B cell maturation and on various B-cell lymphomas and has been identified as a potential therapeutic target for cancer therapy, i.e., the BAFF receptor can be used to specifically target therapeutic molecules to cancer cells. An exemplary amino acid sequence of a human BAFF receptor is represented by GenBank Accession No. NP 443177 (SEQ ID NO:18).

As used herein, an antibody that "specifically binds to BAFF receptor" refers to an antibody that binds to a BAFF receptor, preferably a human BAFF receptor, with a KD of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of SEQ ID NOs:3, 4, 5, 6, 7, and 8, respectively; wherein the antibody or antigen-binding fragment thereof specifically binds BAFF receptor, preferably human BAFF receptor.

According to another particular aspect, the invention relates to an isolated monoclonal antibody or antigen-binding fragment thereof comprising a heavy chain variable region having a polypeptide sequence at least 85%, preferably 90%, more preferably 95% or more, such as 95%, 96%, 97%, 98%, or 99% identical to one of SEQ ID NO:1, or a light chain variable region having a polypeptide sequence at least 85%, preferably 90%, more preferably 95% or more, such as 95%, 96%, 97%, 98%, or 99% identical to one of SEQ ID NO:2.

According to one preferred embodiment, the isolated monoclonal antibody or antigen-binding fragment thereof of the invention comprises a heavy chain variable region having the polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2, respectively.

According to another particular aspect, the invention relates to an isolated monoclonal antibody or antigen-binding fragment thereof of the invention, comprising a heavy chain variable region having the polypeptide sequence of SEQ ID NO:1, and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:3, 4, 5, 6, 7, and 8, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

According to another particular aspect, the invention relates to an isolated monoclonal antibody or antigen-binding fragment thereof, wherein the antibody or antigen-binding fragment thereof has increased stability and/or less immunogenicity in a subject as compared to a control antibody. By way of an example, a control antibody can be another isolated monoclonal antibody that specifically binds BAFF receptor, preferably human BAFF receptor. The control antibody can, for example, comprise a heavy chain complementarity determining region 1 (HCDR1), a HCDR2, a HCDR3, a light chain complementarity determining region 1 (LCDR1), a LCDR2, and a LCDR3, having the polypeptide sequences of SEQ ID NOs:11, 12, 13, 14, 15, and 16, respectively.

According to another particular aspect, the invention relates to an isolated monoclonal antibody or antigen-binding fragment thereof, wherein the antibody or antigen-binding fragment thereof is human or humanized.

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention. Such techniques are well known to those skilled in the art in view of the present disclosure.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated monoclonal antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21$^{st}$ edition (2005), and any later editions). Non-limiting examples of additional ingredients include: buffers, diluents, solvents, tonicity regulating agents, preservatives, stabilizers, and chelating agents. One or more pharmaceutically acceptable carrier can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms may be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Methods of Use

In another general aspect, the invention relates to a method of targeting BAFF receptor on a cancer cell surface in a subject, the method comprising administering to the subject an isolated monoclonal antibody or antigen binding fragment thereof that specifically binds BAFF receptor or a pharmaceutical composition of the invention. Binding of the monoclonal antibody or antigen-binding fragment thereof to BAFF receptor can mediate complement-dependent cytotoxicity (CDC), antibody-dependent phagocytosis (ADPC), and/or antibody-dependent cellular cytotoxicity (ADCC) or other effects that result in the death of the targeted cancer cell. The monoclonal antibody or antigen-binding fragment thereof can, for example, serve to recruit conjugated drugs, and/or can form a bispecific antibody with another monoclonal antibody to mediate the death of the targeted cancer cell.

The functional activity of antibodies and antigen-binding fragments thereof that bind BAFF receptor can be characterized by methods known in the art and as described herein. Methods for characterizing antibodies and antigen-binding fragments thereof that bind BAFF receptor include, but are not limited to, affinity and specificity assays including Biacore, ELISA, and OctetRed analysis; binding assays to detect the binding of antibodies to BAFF receptor on cancer cells or cells recombinantly expressing BAFF receptor by FACS. According to particular embodiments, the methods for characterizing antibodies and antigen-binding fragments thereof that bind BAFF receptor include those described below.

In another general aspect, the invention relates to a method of treating a cancer in a subject in need thereof, comprising administering to the subject an isolated monoclonal antibody or antigen binding fragment thereof that specifically binds BAFF receptor or a pharmaceutical composition of the invention. In certain embodiments, the cancer is a lymphoma, a leukemia, or a myeloma. The cancer can be selected from any liquid or solid cancer, for example, it can be selected from, but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CIVIL), a multiple myeloma (MM), an acute myeloid leukemia (AML), and other liquid tumors. The non-Hodgkin's lymphoma (NHL) can, for example, be a mantle cell lymphoma, a follicular lymphoma, a diffuse large B-cell lymphoma, a marginal zone lymphoma, or a Burkitt's lymphoma.

According to embodiments of the invention, the pharmaceutical composition comprises a therapeutically effective amount of an anti-BAFF receptor antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-BAFF receptor antibodies or antigen-binding fragments thereof, a therapeutically effective amount means an amount of the anti-BAFF receptor antibody or antigen-binding fragment thereof that modulates an immune response in a subject in need thereof.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, provided are compositions used in the treatment of a cancer. For cancer therapy, the compositions can be used in combination with another treatment including, but not limited to, a chemotherapy, an anti-CD20 mAb, an anti-CD47 mAb, an anti-CD73 mAb, an anti-apelin mAb, an anti-CTLA-4 mAb, an anti-PD-L1 mAb, an anti-PD-1 mAb, a PD-1/PD-L1 therapy, other immuno-oncology drugs, an antiangiogenic agent, a radiation therapy, an antibody-drug conjugate (ADC), a targeted therapy, or other anticancer drugs. Anti-BAFF receptor antibodies can be used to construct bispecific antibodies with partner mAbs against PD-1, PD-L1, CTLA-4, EGFR, HER-2, CD19, CD20, CD33, CD73, CD47, CD3, and/or other tumor surface antigens to treat cancers/tumors that express both BAFF receptor and the specific tumor associated antigen.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of determining a level of BAFF receptor in a subject. The methods comprise (a) obtaining a sample from the subject; (b) contacting the sample with a monoclonal antibody or antigen-binding fragment thereof of the invention; and (c) determining a level of BAFF receptor in the subject.

As used herein, "sample" refers to a biological sample isolated from a subject and can include, but is not limited to, whole blood, serum, plasma, blood cells, endothelial cells, tissue biopsies (e.g., a cancer tissue), lymphatic fluid, ascites fluid, interstitial fluid, bone marrow, cerebrospinal fluid, saliva, mucous, sputum, sweat, urine, or any other secretion, excretion, or other bodily fluids. A "blood sample" refers to whole blood or any fraction thereof, including blood cells, serum, and plasma.

In certain embodiments, the level of BAFF receptor in the subject can be determined utilizing assays selected from, but not limited to, a Western blot assay, an ELISA assay, and/or an immunohistochemistry (IHC). Relative protein levels can be determined by utilizing Western blot analysis and immunohistochemistry (IHC), and absolute protein levels can be determined by utilizing an ELISA assay. When determining the relative levels of BAFF receptor, the levels of BAFF receptor can be determined between at least two samples, e.g., between samples from the same subject at different time points, between samples from different tissues in the same subject, and/or between samples from different subjects. Alternatively, when determining absolute levels of BAFF receptor, such as by an ELISA assay, the absolute level of BAFF receptor in the sample can be determined by creating a standard for the ELISA assay prior to testing the sample. A person skilled in the art would understand which analytical techniques to utilize to determine the level of BAFF receptor in a sample from the subject utilizing the antibodies or antigen-binding fragments thereof of the invention.

Utilizing methods of determining a level of BAFF receptor in a sample from a subject can lead to the diagnosis of abnormal (elevated, reduced, or insufficient) BAFF receptor levels in a disease and making appropriate therapeutic decisions. Such a disease can include, for example, cancer. Additionally, by monitoring the levels of BAFF receptor in a subject, the risk of developing a disease as indicated above can be determined based on the knowledge of the level of BAFF receptor in a particular disease and/or during the progression of the particular disease.

EMBODIMENTS

This application provides the following non-limiting embodiments.

Embodiment 1 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequence of SEQ ID NOs:3, 4, 5, 6, 7, and 8, respectively; wherein the antibody or antigen-binding fragment thereof specifically binds BAFF receptor, preferably human BAFF receptor.

Embodiment 2 is the isolated monoclonal antibody or antigen-binding fragment thereof of embodiment 1, comprising a heavy chain variable region having a polypeptide sequence at least 95%, at least 96%, at least 97%, at least 98%, or at least 99% identical to SEQ ID NO:1, and a light chain variable region having a polypeptide sequence at least 95%, at least 96%, at least 97%, at least 98%, or at least 99% identical to SEQ ID NO:2.

Embodiment 3 is the isolated monoclonal antibody or antigen-binding fragment thereof of embodiment 1 or 2, comprising a heavy chain variable region having the polypeptide sequence of SEQ ID NO:1, and a light chain variable region having the polypeptide sequence of SEQ ID NO:2.

Embodiment 4 is the isolated monoclonal antibody or antigen-binding fragment thereof of any one of embodiments 1 to 3, wherein the antibody or antigen-binding fragment thereof has increased stability and/or less immunogenicity in a subject as compared to a control antibody.

Embodiment 5 is the isolated monoclonal antibody or antigen-binding fragment thereof of any one of embodiments 1 to 4, wherein the antibody or antigen-binding fragment thereof is human or humanized.

Embodiment 6 is an isolated monoclonal antibody or antigen-binding fragment thereof of any one of embodiments 1 to 5, wherein the monoclonal antibody or antigen-binding fragment thereof is capable of binding BAFF receptor and inducing effector-mediated tumor cell lysis.

Embodiment 7 is an isolated nucleic acid encoding the monoclonal antibody or antigen-binding fragment thereof of any one of embodiments 1 to 6.

Embodiment 8 is a vector comprising the isolated nucleic acid of embodiment 7.

Embodiment 9 is a host cell comprising the vector of embodiment 8.

Embodiment 10 is a pharmaceutical composition, comprising the isolated monoclonal antibody or antigen-binding fragment thereof of any one of embodiments 1 to 6 and a pharmaceutically acceptable carrier.

Embodiment 11 is a method of treating cancer in a subject in need thereof, comprising administering to the subject the pharmaceutical composition of embodiment 10.

Embodiment 12 is a method of targeting BAFF receptor on a cancer cell surface in a subject in need thereof, the method comprising administering to the subject the pharmaceutical composition of embodiment 10.

Embodiment 13 is a method of producing the monoclonal antibody or antigen-binding fragment thereof of any one of embodiments 1 to 6, comprising culturing a cell comprising a nucleic acid encoding the monoclonal antibody or antigen-binding fragment thereof under conditions to produce the monoclonal antibody or antigen-binding fragment thereof and recovering the monoclonal antibody or antigen-binding fragment thereof from the cell or culture.

Embodiment 14 is a method of producing a pharmaceutical composition comprising the monoclonal antibody or antigen-binding fragment of any one of embodiments 1 to 6, comprising combining the monoclonal antibody or antigen-binding fragment thereof with a pharmaceutically acceptable carrier to obtain the pharmaceutical composition.

Embodiment 15 is a method of determining a level of BAFF receptor in a subject, the method comprising:
 a. obtaining a sample from the subject;
 b. contacting the sample with an isolated monoclonal antibody or antigen-binding fragment thereof of any one of embodiments 1 to 6; and
 c. determining a level of BAFF receptor in the subject.

Embodiment 16 is the method of embodiment 15, wherein the sample is a tissue sample.

Embodiment 17 is the method of embodiment 16, wherein the tissue sample is a cancer tissue sample.

Embodiment 18 is the method of embodiment 15, wherein the sample is a blood sample.

EXAMPLES

Example 1: Identification and Characterization of H90-11, an Affinity Maturated Anti-BAFF Receptor Monoclonal Antibody H90-11, an anti-BAFF receptor monoclonal antibody, was identified from an affinity maturation screen of a previously identified anti-BAFF receptor monoclonal antibody, H90-5 (WO2017/214170; Qin et al., Clin. Canc. Res. 24(5):1114-23 (2018)). H90-11 did not show a significantly improved affinity to BAFF-receptor when compared to H90-5 (Table 1); however, several features of H90-11 were observed, as indicated below.

TABLE 1

Anti-BAFF receptor monoclonal antibody affinity for BAFF receptor

| mAb target | $K_D$ (M) | $K_{on}$ (1/Ms) | $K_{dis}$ (1/s) | Full X^2 | Full R^2 |
|---|---|---|---|---|---|
| H90-5 | 3.4E−09 | 9.9E+05 | 3.4E−03 | 0.0106 | 0.9816 |
| H90-11 | 9.5E−10 | 8.6E+05 | 8.2E−04 | 0.0073 | 0.9927 |

It was noted that H90-11 shared the same heavy chain variable region as H90-5 (SEQ ID NO:1 vs. SEQ ID NO:9, respectively). However, H90-11 and H90-5 comprised different light chain variable regions (SEQ ID NO:2 vs. SEQ ID NO:10, respectively).

Next, it was shown that when utilizing an Ig Blast, H90-5 had 12 different amino acid residues when compared to a human germ line Ig sequence (FIG. 1B), whereas, H90-11 only had 6 different amino acid residues when compared to the same human germ line Ig sequence (FIG. 1A). Given that the H90-11 monoclonal antibody was more similar to a human germ line sequence, it is believed that the H90-11 monoclonal antibody is less likely to induce an immune response in a human. Further, it is believed that the more similar an antibody is to the human germ line sequence, the more stable the antibody will be.

To that end, the stability and immunogenicity of the H90-5 and H90-11 antibodies were assessed. Both H90-5 and H90-11 were produced as full length human IgG1, and the antibody drug rituximab and monoclonal antibody C90, which is the basis for H90-5 prior to being humanized, were produced as antibody controls. The antibodies used for the stability and immunogenicity studies had the following properties, as outlined in Table 2.

TABLE 2

Antibody properties

| Sample ID | EC280 (mL · mg$^{-1}$ · cm$^{-1}$) | Supplied Conc. (mg/mL) | pI |
|---|---|---|---|
| Rituxan | 1.643 | 0.28 | 8.66 |
| C90 | 1.495 | 2.6 | 7.91 |
| H90-5 | 1.500 | 1.9 | 8.24 |
| H90-11 | 1.624 | 1.4 | 8.34 |

Utilizing the standup monolayer adsorption chromatography (SMAC) high-performance liquid chromatography (HPLC) method described in Kohli et al., the stability of the H90-11, H90-5, C90, and Rituxan antibodies was assessed (Kohli et al., mAbs 7(4):752-8 (2015)). Antibodies with a high retention time (e.g., >20 minutes) on a Zenix column will precipitate over time, whereas, antibodies with a low retention time on the Zenix column (e.g., <10 minutes) will not precipitate. Antibodies with a retention time between 10 and 20 minutes require further assessment with different methods.

Briefly, the SMAC-HPLC method utilizes the following HPLC and SMAC column: an Agilent 1100 equipped with DAD for HPLC, and a Zenix SEC-300, 4.6×300 mm, 300 Å, 3 μM column for SMAC. The flow rate of the column was 0.35 mL/min, and the mobile phase comprised 150 mM sodium phosphate at a pH of 7.0. The column was run for 20 minutes. The samples were analyzed at 5° C. at wavelengths of 214 nm and 280 nm, and the column was kept at room temperature. The sample buffer was tris-glycine buffer (100 mM Tris/90 mM glycine, pH 7.5). 3 μg of sample was loaded in each column.

SMAC retention time (RT) is inversely related to colloidal stability. Proteins retained longer on the column with broader peaks are prone to aggregation or precipitation. The aggregation propensity of H90-11 was low (RT<10 minutes), which was similar to Rituxan, whereas, the aggregation propensity of C90 and its humanized version H90-5 was intermediate (RT>10 minutes). Thus, H90-11 was considered less prone to aggregation than H90-5. Results of the SMAC-HPLC studies are shown in FIGS. 2A-2D and Table 3 below.

TABLE 3

Summary of SMAC-results

| | Monomer | | HMWS | | LMWS | |
|---|---|---|---|---|---|---|
| Sample | RT | % RPA | RT | % RPA | RT | % RPA |
| Rituxan | 7.9 | 100 | — | — | — | — |
| C90 | 10.7 | 95.3 | 7.7 | 2.6 | 12.9 | 2.1 |
| H90-5 | 11.3 | 99.2 | — | — | 13.6 | 0.8 |
| H90-11 | 8.2 | 99.6 | 6.7 | 0.4 | — | — |

Figure 3:
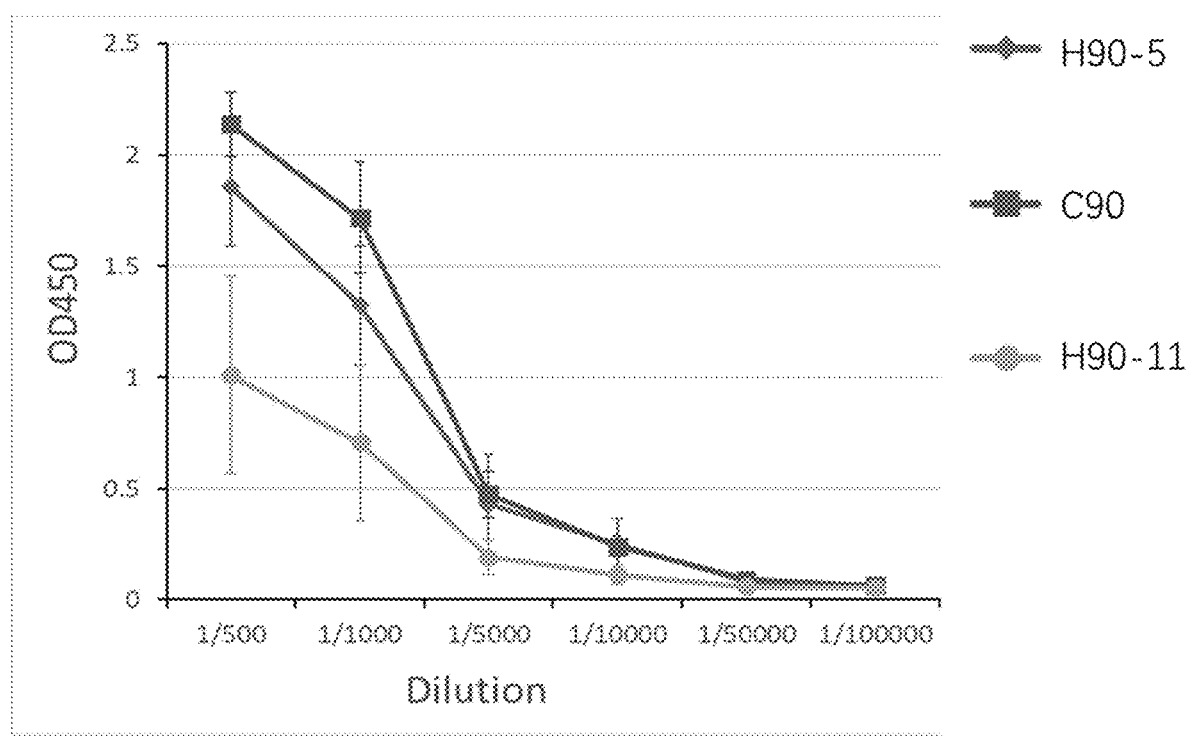
FIG. 3 shows the results of the immunogenicity of the H90-5, H90-11, and C90 mAbs as measured utilizing an indirect ELISA assay.

Utilizing an AI-powered immunogenicity prediction and assessment system, established by Sun et al., (Sun et al., J. Immunol. Methods 452:6-11 (2018)), the immunogenicity of the H90-11, H90-5, and C90 antibodies was assessed. Briefly, Balb/c mice were used to evaluate the anti-drug-antibody titer of different antibodies. ~4 to 6-week old female Balb/c mice were first immunized with antibodies in Complete Freund's Adjuvant and boosted with antibodies in incomplete Freund's Adjuvant. Four weeks following the first immunization, blood was obtained from the tails of immunized mice and was tested for antibody titers against the immunized antibody by indirect Enzyme-linked Immunoassay (ELISA), as described in Sun et al., to assess the potential immunogenicity of H90-11 and H90-5. It was observed that H90-11 had lower anti-drug antibodies in mice than H90-5 (FIG. 3). Thus, it is believed that H90-11 would have a lower immunogenicity in humans than H90-5.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequence of:

a. SEQ ID NOs:3, 4, 5, 6, 7, and 8, respectively;

wherein the antibody or antigen-binding fragment thereof specifically binds B-cell activating factor (BAFF) receptor.

2. The isolated monoclonal antibody or antigen-binding fragment thereof of claim 1, comprising a heavy chain variable region having a polypeptide sequence at least 95%, at least 96%, at least 97%, at least 98%, or at least 99% identical to SEQ ID NO:1, and a light chain variable region having a polypeptide sequence at least 95%, at least 96%, at least 97%, at least 98%, or at least 99% identical to SEQ ID NO:2.

3. The isolated monoclonal antibody or antigen-binding fragment thereof of claim 1, comprising a heavy chain variable region having the polypeptide sequence of SEQ ID NO:1, and a light chain variable region having the polypeptide sequence of SEQ ID NO:2.

4. The isolated monoclonal antibody or antigen-binding fragment thereof of claim 1, wherein the antibody or antigen-binding fragment thereof has increased stability and/or less immunogenicity in a subject as compared to a control antibody.

5. The isolated monoclonal antibody or antigen-binding fragment thereof of claim 1, wherein the antibody or antigen-binding fragment thereof is humanized.

6. The isolated monoclonal antibody or antigen-binding fragment thereof of claim 1, wherein the monoclonal antibody or antigen-binding fragment thereof is capable of binding BAFF receptor and inducing effector-mediated tumor cell lysis.

7. The isolated monoclonal antibody or antigen-binding fragment thereof of claim 1, wherein the BAFF receptor is a human BAFF receptor.

8. A pharmaceutical composition, comprising the isolated monoclonal antibody or antigen-binding fragment thereof of claim 1 and a pharmaceutically acceptable carrier.

9. A method of treating cancer in a subject in need thereof, wherein the cancer is a lymphoma, a myeloma, or a leukemia, comprising administering to the subject the pharmaceutical composition of claim 8.

10. A method of targeting BAFF receptor on a cancer cell surface in a subject in need thereof, the method comprising administering to the subject the pharmaceutical composition of claim 8.

11. A method of producing a pharmaceutical composition comprising the monoclonal antibody or antigen-binding fragment of claim 1, comprising combining the monoclonal antibody or antigen-binding fragment thereof with a pharmaceutically acceptable carrier to obtain the pharmaceutical composition.

* * * * *

SEQUENCE LISTING

<160> NUMBER OF SEQ ID NOS: 19

<210> SEQ ID NO 1
<211> LENGTH: 118
<212> TYPE: PRT
<213> ORGANISM: Artificial Sequence

```
<220> FEATURE:
<223> OTHER INFORMATION: H90-11 Variable Heavy Chain

<400> SEQUENCE: 1

Glu Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Ile
        35                  40                  45

Gly Tyr Ile Ser Tyr Ser Gly Ser Thr Tyr Tyr Asn Pro Ser Leu Lys
    50                  55                  60

Ser Arg Val Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Ser Pro Asn Tyr Pro Phe Tyr Ala Met Asp Tyr Trp Gly Gln Gly Thr
            100                 105                 110

Leu Val Thr Val Ser Ser
        115

<210> SEQ ID NO 2
<211> LENGTH: 114
<212> TYPE: PRT
<213> ORGANISM: Artificial Sequence
<220> FEATURE:
<223> OTHER INFORMATION: H90-11 Variable Light Chain

<400> SEQUENCE: 2

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Thr Pro Trp Thr Phe Gly Gln Gly Thr Lys Leu Glu Ile
            100                 105                 110

Lys Arg

<210> SEQ ID NO 3
<211> LENGTH: 8
<212> TYPE: PRT
<213> ORGANISM: Artificial Sequence
<220> FEATURE:
<223> OTHER INFORMATION: H90-11 HCDR1

<400> SEQUENCE: 3

Gly Asp Ser Ile Thr Ser Gly Tyr
1               5

<210> SEQ ID NO 4
<211> LENGTH: 7
<212> TYPE: PRT
```

<213> ORGANISM: Artificial Sequence
<220> FEATURE:
<223> OTHER INFORMATION: H90-11 HCDR2

<400> SEQUENCE: 4

Ile Ser Tyr Ser Gly Ser Thr
1               5

<210> SEQ ID NO 5
<211> LENGTH: 12
<212> TYPE: PRT
<213> ORGANISM: Artificial Sequence
<220> FEATURE:
<223> OTHER INFORMATION: H90-11 HCDR3

<400> SEQUENCE: 5

Ala Ser Pro Asn Tyr Pro Phe Tyr Ala Met Asp Tyr
1               5                   10

<210> SEQ ID NO 6
<211> LENGTH: 8
<212> TYPE: PRT
<213> ORGANISM: Artificial Sequence
<220> FEATURE:
<223> OTHER INFORMATION: H90-11 LCDR1

<400> SEQUENCE: 6

Gln Ser Val Leu Tyr Ser Ser Asn
1               5

<210> SEQ ID NO 7
<211> LENGTH: 3
<212> TYPE: PRT
<213> ORGANISM: Artificial Sequence
<220> FEATURE:
<223> OTHER INFORMATION: H90-11 LCDR2

<400> SEQUENCE: 7

Trp Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: H90-11 LCDR3

<400> SEQUENCE: 8

Gln Gln Ser Tyr Ser Thr Pro Trp Thr
1               5

<210> SEQ ID NO 9
<211> LENGTH: 118
<212> TYPE: PRT
<213> ORGANISM: Artificial Sequence
<220> FEATURE:
<223> OTHER INFORMATION: H90-5 Variable Heavy Chain

<400> SEQUENCE: 9

Glu Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Ile
        35                  40                  45

```
Gly Tyr Ile Ser Tyr Ser Gly Ser Thr Tyr Tyr Asn Pro Ser Leu Lys
        50                  55                  60

Ser Arg Val Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Ser Pro Asn Tyr Pro Phe Tyr Ala Met Asp Tyr Trp Gly Gln Gly Thr
                100                 105                 110

Leu Val Thr Val Ser Ser
            115

<210> SEQ ID NO 10
<211> LENGTH: 112
<212> TYPE: PRT
<213> ORGANISM: Artificial Sequence
<220> FEATURE:
<223> OTHER INFORMATION: H90-5 Variable Light Chain

<400> SEQUENCE: 10

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Ile Ser Phe Met Asn Trp Phe Gln Gln Lys Pro Gly Gln Ala Pro
            35                  40                  45

Arg Leu Leu Ile Tyr Ala Ala Ser Asn Arg Ala Thr Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Val Pro Trp Thr Phe Gly Gly Gly Thr Lys Val Glu Ile Lys Arg
                100                 105                 110

<210> SEQ ID NO 11
<211> LENGTH: 8
<212> TYPE: PRT
<213> ORGANISM: Artificial Sequence
<220> FEATURE:
<223> OTHER INFORMATION: H90-5 HCDR1

<400> SEQUENCE: 11

Gly Asp Ser Ile Thr Ser Gly Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: H90-5 HCDR2

<400> SEQUENCE: 12

Ile Ser Tyr Ser Gly Ser Thr
1               5

<210> SEQ ID NO 13
<211> LENGTH: 12
<212> TYPE: PRT
<213> ORGANISM: Artificial Sequence
<220> FEATURE:
```

```
<223> OTHER INFORMATION: H90-5 HCDR3

<400> SEQUENCE: 13

Ala Ser Pro Asn Tyr Pro Phe Tyr Ala Met Asp Tyr
1               5                   10

<210> SEQ ID NO 14
<211> LENGTH: 6
<212> TYPE: PRT
<213> ORGANISM: Artificial Sequence
<220> FEATURE:
<223> OTHER INFORMATION: H90-5 LCDR1

<400> SEQUENCE: 14

Glu Ser Val Asp Asn Tyr
1               5

<210> SEQ ID NO 15
<211> LENGTH: 3
<212> TYPE: PRT
<213> ORGANISM: Artificial Sequence
<220> FEATURE:
<223> OTHER INFORMATION: H90-5 LCDR2

<400> SEQUENCE: 15

Ala Ala Ser
1

<210> SEQ ID NO 16
<211> LENGTH: 9
<212> TYPE: PRT
<213> ORGANISM: Artificial Sequence
<220> FEATURE:
<223> OTHER INFORMATION: H90-5 LCDR3

<400> SEQUENCE: 16

Gln Gln Ser Lys Glu Val Pro Trp Thr
1               5

<210> SEQ ID NO 17
<211> LENGTH: 114
<212> TYPE: PRT
<213> ORGANISM: Artificial Sequence
<220> FEATURE:
<223> OTHER INFORMATION: Human IGKV4-1*01

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Leu Glu Ile
            100                 105                 110

Lys Arg
```

```
<210> SEQ ID NO 18
<211> LENGTH: 184
<212> TYPE: PRT
<213> ORGANISM: Artificial Sequence
<220> FEATURE:
<223> OTHER INFORMATION: Human BAFF receptor

<400> SEQUENCE: 18

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Arg Gln Arg Arg Leu Arg Gly Ala Ser
            100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
    130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180

<210> SEQ ID NO 19
<211> LENGTH: 95
<212> TYPE: PRT
<213> ORGANISM: Artificial Sequence
<220> FEATURE:
<223> OTHER INFORMATION: Human IGKV3-11*01

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```